United States Patent [19]

Buchecker et al.

[11] Patent Number: 5,582,767
[45] Date of Patent: Dec. 10, 1996

[54] FLUOROSUBSTITUTED TOLANE DERIVATIVES

[75] Inventors: Richard Buchecker, Zurich; Martin Schadt, Seltisberg, both of Switzerland

[73] Assignee: Hoffmann-La Roche Inc., Nutley, N.J.

[21] Appl. No.: 148,720

[22] Filed: Nov. 8, 1993

[30] Foreign Application Priority Data

Nov. 16, 1992 [CH] Switzerland .............. 3520/92

[51] Int. Cl.$^6$ .......................... C09K 19/12; C07C 19/08; C07C 22/00; G02F 1/13
[52] U.S. Cl. ............... 252/299.66; 570/127; 570/144; 570/128; 252/299.01; 349/182
[58] Field of Search .............. 252/299.66, 299.01; 570/127, 128

[56] References Cited

U.S. PATENT DOCUMENTS

| | | | |
|---|---|---|---|
| 5,068,053 | 11/1991 | Reiffenrath et al. | 252/299.61 |
| 5,154,851 | 10/1992 | Goto et al. | 252/299.63 |
| 5,194,178 | 3/1993 | Coates et al. | 252/299.63 |
| 5,207,944 | 5/1993 | Sawada et al. | 252/299.01 |
| 5,242,618 | 9/1993 | Krause et al. | 252/299.6 |
| 5,250,216 | 10/1993 | Goto et al. | 252/299.6 |
| 5,314,640 | 5/1994 | Yamada et al. | 252/299.6 |
| 5,356,558 | 10/1994 | Yamada et al. | 252/299.01 |
| 5,372,746 | 12/1994 | Buchecker et al. | 252/299.61 |
| 5,399,292 | 5/1995 | Buchecker et al. | 252/299.63 |
| 5,422,035 | 6/1995 | Bartmann et al. | 252/299.01 |

FOREIGN PATENT DOCUMENTS

| | | |
|---|---|---|
| 4000535 | 6/1991 | Germany . |
| 4105742 | 8/1992 | Germany . |
| 88/07523 | 10/1988 | WIPO . |
| 88/07514 | 10/1988 | WIPO . |

OTHER PUBLICATIONS

Derwent Abstract 92–293267/36 (1992) for DE 4105742.
Derwent Abstract 91–179085/26 (1991) for DE 4000535.

*Primary Examiner*—C. H. Kelly
*Attorney, Agent, or Firm*—George W. Johnston; Robert A. Silverman

[57] ABSTRACT

The invention relates to liquid crystalline, multiply-substituted fluorinated tolane derivatives, their preparation, liquid crystalline mixtures which comprise such compounds and the use of these compounds and mixtures for electro-optical purposes.

12 Claims, No Drawings

FLUOROSUBSTITUTED TOLANE DERIVATIVES

SUMMARY OF THE INVENTION

The invention is concerned with a compound of the formula

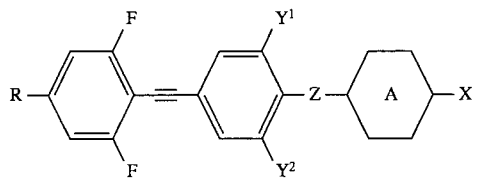

wherein

R is alkyl, alkoxy, alkenyl or alkenyloxy with up to 12 carbon atoms in which one $CH_2$ group can be replaced by oxygen and/or one or more hydrogen atoms can be replaced by fluorine atoms, with the proviso that two oxygen atoms are not directly adjacent;

$Y^1$, $Y^2$ each independently are fluorine or hydrogen;

A is trans-1,4-cyclohexylene or optionally fluoro-substituted 1,4-phenylene;

Z is a single covalent bond, —$CH_2CH_2$—, —$OCH_2$—, —$CH_2O$—, —$(CH_2)_4$—, —$O(CH_2)_3$—, or —$(CH_2)_3O$—, and when ring A represents a saturated ring, Z can also be the trans form of —$(CH_2)_2CH$=CH— or —$CH_2OCH$=CH—; and X is alkyl, alkenyl, alkoxy, alkenyloxy, alkoxyalkyl with up to 6 carbon atoms, or —CH=$CF_2$, and when A is trans-1,4-cyclohexylene X can also be —CH=CHCl or —CH=CHF, and when A is 1,4-phenylene X can also be fluorine, chlorine, —$CF_3$, —$OCF_3$ or —$OCHF_2$.

The invention is also concerned with liquid a crystalline mixture comprising at least two components, a first component being a compound of formula I and a second component and optionally further components being additional compounds of formula I and/or other liquid crystal components selected from a group consisting of compounds of the formulas

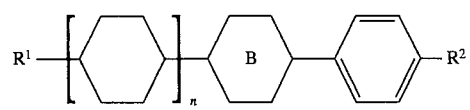

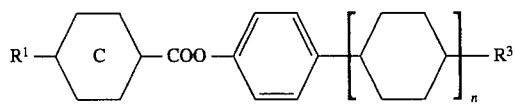

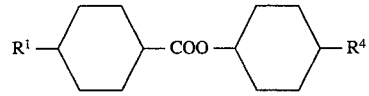

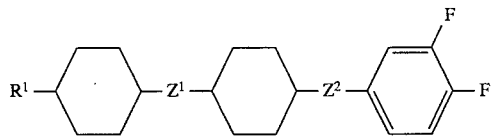

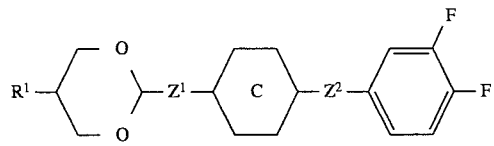

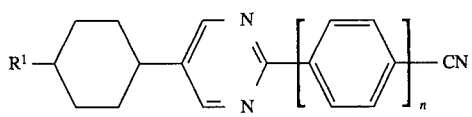

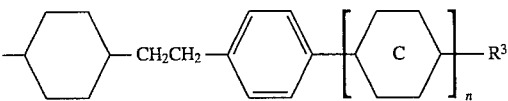

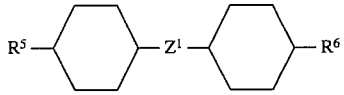

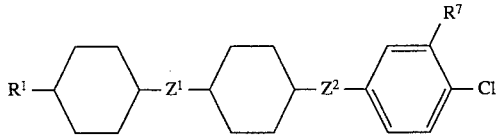

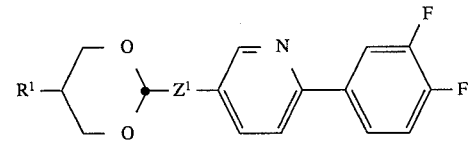

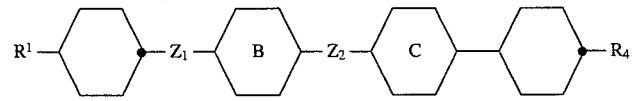

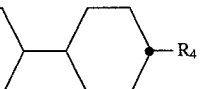

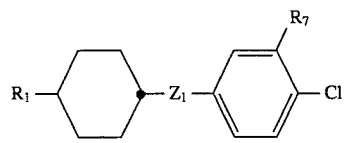

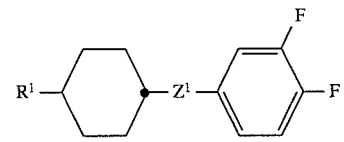

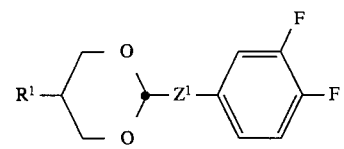

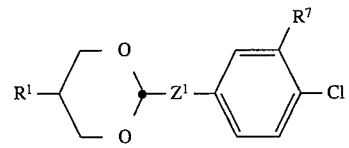

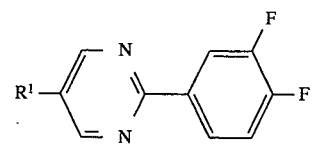
XIX

XX

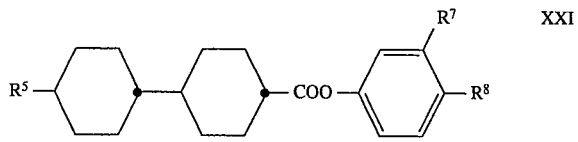
XXI

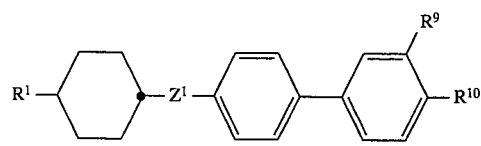
XXII wherein $R^1$, $R^4$ is alkyl, alkoxyalkyl, 3E-alkenyl, 4-alkenyl or on saturated rings also 1E-alkenyl;

n is 0 or 1;

ring B is 1,4-phenylene, pyridine-2,5-diyl, pyrimidine-2,5-diyl, trans-1,4-cyclohexylene or trans-1,3-dioxane-2,5-diyl;

$R^2$ is cyano, isothiocyanto, fluorine, alkyl, 3E-alkenyl, 4-alkenyl, alkoxy, 2E-alkenyloxy, 3-alkenyloxy or 1-alkynyl;

ring C is 1,4-phenylene or trans-1,4-cyclohexylene;

$R^3$ is alkyl, 3E-alkenyl, 4-alkenyl or when Ring C is trans-1,4-cyclohexylene also 1E-alkenyl, or when Ring C is 1,4-phenylene also cyano, isothiocyanato, alkoxy, 2E-alkenyloxy or 3-alkenyloxy;

$R^5$ is alkyl, 1E-alkenyl, 3E-alkenyl or 4-alkenyl;

$R^6$ is cyano, alkyl, 1E-alkenyl, 3E-alkenyl, 4-alkenyl, alkoxy, 2E-alkenyloxy, 3-alkenyloxy, alkoxymethyl or (2E-alkenyl)oxymethyl;

$Z^1$, $Z^2$ each independently is a single covalent bond or —$CH_2CH_2$—, with two aromatic rings always being linked by a single covalent bond;

$R^7$ is hydrogen, fluorine or chlorine;

$R^8$ is cyano, fluorine or chlorine;

$R^9$ is hydrogen or fluorine; and $R^{10}$ is fluorine or chlorine.

BACKGROUND OF THE ART

Liquid crystals are used primarily as dielectrics in indicating devices, since the optical properties of such substances can be influenced by an applied voltage. Electro-optical devices based on liquid crystals are well-known to a person skilled in the art and can be based on various effects. Such devices are, for example, cells having dynamic scattering, DAP cells (deformation of aligned phases), guest/host cells, TN cells having a twisted nematic structure, STN cells ("super twisted nematic"), SBE cells ("super birefringence effect") and OMI cells ("optical mode interference"). For displays having a high density of information, actively controlled cells, for example TFT cells ("thin film transistor"), have recently become especially important in addition to the passively controlled, multiplexed cells. The most common indicating devices are based on the Schadt-Helfrich effect and have a twisted nematic structure.

The liquid crystal materials must have a good chemical, photochemical and thermal stability and a good stability towards electric fields. Further, they should have not only a suitable mesophase over a range which is as broad as possible (for example, a nematic or cholesteric phase for the aforementioned cells), but also a sufficiently low viscosity and in the cells should permit short response times, low threshold potentials and a high contrast. Further properties such as the electrical conductivity, the dielectric anisotropy and the optical anisotropy must fulfil different requirements depending on the field of application and type of cell. For example, materials for cells having a twisted nematic structure should have a positive dielectric anisotropy which is as high as possible and simultaneously should have a conductivity which is as low as possible. This latter property is especially important primarily for TFT cells. Unfortunately, however, liquid crystal materials having a high dielectric anisotropy lead mainly to an increased conductivity in mixtures as a result of their improved capability of dissolving ionic impurities. Accordingly, a need exists for liquid crystal materials which have a dielectric anisotropy which is as high as possible with a conductivity which is as low as possible.

DETAILED DESCRIPTION OF THE INVENTION

The compounds in accordance with the invention are liquid crystals having a pronounced nematic tendency which lead only to insignificant clearing point depressions in mixtures, even when they are isotropic. They are distinguished by a high dielectric anisotropy, a relatively low rotation viscosity and therefore comparatively low threshold potentials and short response times. The conductivity is relatively low in spite of the high dielectric anisotropy. Moreover, in spite of multiple lateral substitution the clearing point of the compounds is surprisingly high with a comparatively low melting point and small melting enthalpy. The relatively high anisotropy can be lowered or increased according to desire by suitable choice of a saturated or aromatic ring for A.

The compounds in accordance with the invention have a very good solubility in mixtures and in broad concentration ranges. They are especially suitable for use in mixtures which, in the case of a low threshold potential, should have a low conductivity and simultaneously a comparatively high optical anisotropy, for example TN, STN or TFT cells having a small layer density or having an especially high contrast, as are required, for example, for projection displays.

The invention is concerned with a compound of the formula

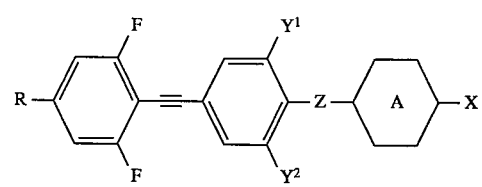
I wherein

R is alkyl, alkoxy, alkenyl or alkenyloxy with up to 12 carbon atoms in which one $CH_2$ group can be replaced by oxygen and/or one or more hydrogen atoms can be replaced by fluorine atoms, with the proviso that two oxygen atoms are not directly adjacent;

$Y^1$, $Y^2$ each independently are fluorine or hydrogen;

A is trans-1,4-cyclohexylene or optionally fluoro-substituted 1,4-phenylene;

Z is a single covalent bond, $-CH_2CH_2-$, $-OCH_2-$, $-CH_2O-$, $-(CH_2)_4-$, $-O(CH_2)_3-$, or $-(CH_2)_3O-$, and when ring A represents a saturated ring, Z can also be the trans form of $-(CH_2)_2CH=CH-$ or $-CH_2OCH=CH-$; and X is alkyl, alkenyl, alkoxy, alkenyloxy, alkoxyalkyl with up to 6 carbon atoms, or $-CH=CF_2$, and when A is trans-1,4-cyclohexylene X can also be $-CH=CHCl$ or $-CH=CHF$, and when A is 1,4-phenylene X can also be fluorine, chlorine, $-CF_3$, $-OCF_3$ or $-OCHF_2$.

In the above compounds of formula I, the term "alkyl, alkoxy, alkenyl or alkenyloxy with up to 12 carbon atoms in which one $CH_2$ group can be replaced by oxygen and/or one or more hydrogen atoms can be replaced by fluorine atoms, with the proviso that two oxygen atoms are not directly adjacent" includes a straight-chain or branched, optionally chiral alkyl, alkoxy, alkenyl, alkenyloxy, alkoxyalkyl, alkenyloxyalkyl or alkyloxyalkenyl residue with up to 12 carbon atoms which can be mono- or multiply-substituted with fluorine. Unsubstituted, straight-chain residues with up to 6 carbon atoms are most preferred. Preferred alkenyl residues are those in which the double bond has the E configuration and is situated at C(3) or, when ring $A^1$ represents a saturated ring, also at C(1) or terminal. Preferred alkenyloxy residues are those having a double bond at C(2) with the E configuration or those having a terminal double bond. Examples of preferred residues are methyl, ethyl, propyl, butyl, pentyl, hexyl, methoxy, ethoxy, propyloxy, butyloxy, pentyloxy, hexyloxy, vinyl, 1E-propenyl, 1E-butenyl, 1E-pentenyl, 1E-hexenyl, 3-butenyl, 3E-pentenyl, 3E-hexenyl, 4-pentenyl, 5-hexenyl, allyloxy, 2E-butenyloxy, 3-butenyloxy, methoxymethyl, ethoxymethyl, propyloxymethyl, allyloxymethyl, methoxyethyl, ethoxyethyl, propyloxyethyl, methoxypropyl, ethoxypropyl, methoxy-1E-propenyl, ethoxy-1E-propenyl and the like.

The term "optionally fluoro-substituted 1,4-phenylene," includes in connection with ring A unsubstituted, mono- or difluorinated 1,4-phenylene rings.

The bridging member Z is preferably a single covalent bond, $-CH_2CH_2-$, $-OCH_2-$ or $-CH_2O-$, especially a single covalent bond or $-CH_2CH_2-$.

In the compounds of formula I in which X is alkyl, alkoxy or alkoxyalkyl, straight-chain residues with up to 6 carbon atoms are preferred, especially with up to 3 carbon atoms, such as, for example, methyl, ethyl, propyl, methoxy, ethoxy, propyloxy, methoxymethyl, ethoxymethyl, methoxyethyl and the like.

In the compounds of formula I in which X is alkenyl or alkenyloxy, straight-chain residues with 2 to 6 carbon atoms are preferred. Most preferred alkenyl residues are those in which the double bond is terminal or has the E configuration and is situated at C(3) or, on a trans-1,4-cyclohexylene ring, also at C(1). Most preferred alkenyloxy residues are those having a double bond at C(2) with the E configuration or those having a terminal double bond. Examples of preferred residues are vinyl, 1E-propenyl, 1E-butenyl, 1E-pentenyl, 1E-hexenyl, 3-butenyl, 3E-pentenyl, 3E-hexenyl, 4-pentenyl, 5-hexenyl, allyloxy, 2E-butenyloxy, 3-butenyloxy and the like.

Especially preferred sub-groups of compounds of formula I are compounds of the formulas

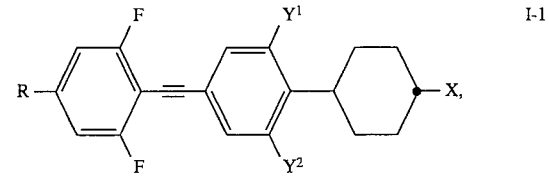

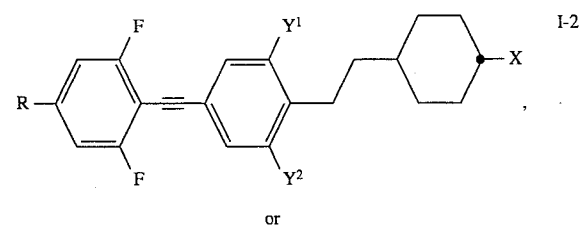

or

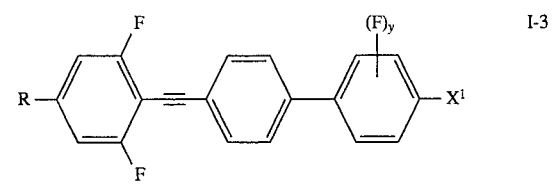

wherein

R is straight-chain alkyl, alkoxy, alkenyl or alkenyloxy with up to 6 carbon atoms in which one $CH_2$ group can be replaced by oxygen, with the proviso that two oxygen atoms are not directly adjacent;

$Y^1$, $Y^2$ each independently are fluorine or hydrogen;

X is alkyl, alkenyl, alkoxy or alkenyloxy with up to 3 carbon atoms, $-CH=CF_2$, $-CH=CHCl$ or $-CH=CHF$;

$X^1$ is fluorine, chlorine, $-OCF_3$, $-OCHF_2$, $-CH=CF_2$ or alkyl, alkenyl, alkoxy or alkenyloxy with up to 3 carbon atoms;

y is 0, 1 or 2;

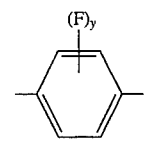

is unsubstituted or substituted as follows

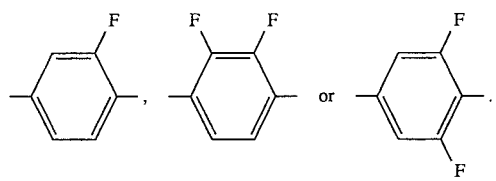

The substituents $Y^1$ and $Y^2$ in formula I, and formulas I-1 and I-2 can be different from one another. Those compounds in which one of these substituents is hydrogen and the other is fluorine or hydrogen are preferred. However, those compounds in which not only $Y^1$ but also $Y^2$ is hydrogen are especially preferred.

Particularly preferred compounds of formula I-3 are those in which $X^1$ is fluorine, chlorine or alkyl with 1 to 3 carbon atoms.

Further, particularly preferred compounds of formula I are compounds of formulae I-1 and I-2 in which X is alkyl or alkenyl with up to 3 carbon atoms, for example methyl, ethyl propyl, vinyl, 1E-propenyl, or —CH=CF$_2$, —CH=CHCl or —CH=CHF.

The preparation of the compounds of formula I can be effected in a manner known per se. In Scheme 1, the substituents given in formulas I–III have the aforementioned significance. The halogenation of a compound IIa with bromine or iodine to compounds of formula III is preferably carried out in an inert solvent such as tetrahydrofuran, ether, dimethoxyethane etc. at a low temperature such as −70° to −40° C.

Metal-catalyzed couplings of phenyl compounds with acetylenes, as presented in the following Scheme for the preparation of I from III, are basically known from the literature, for example C. Pogh and V. Percey, *Mol. Cryst. Liq. Cryst.* (1990) 178, 193. As previously mentioned, they can be carried out with bromides or iodides, but in certain instances also with trifluorosulfonates or chlorides. Thus, a compound of formula III is firstly reacted, for example, with 2-methyl-3-butyn-2-ol in an inert solvent such as, for example, tetrahydrofuran using catalytic amounts of bis-triphenylphosphine-palladium chloride, copper-1 iodide and triphenyl-phosphine in the presence of triethylamine at an elevated temperature, preferably the reflux temperature of the reaction mixture. Thereafter, potassium hydroxide and tetrabutylammonium hydrogen sulfate as well as the compound of type IIb are added and left to react at an elevated temperature until the reaction has finished. In the case of the compounds of type IIb there can also be used, in place of bromides, basically analogous iodides, trifluoromethylsulfonates and homologous polyfluoroalkylsulfonates. Usually, the mono-coupled acetylene IIIa is isolated, the protecting group (isopropyloxy in this case) is cleaved off and in a next step coupling with a compound of general formula IIb may be carried out. The conversion of intermediates of formula III into compounds of formula I can, however, also be realized in one step, that is without the intermediate isolation of the compound of formula IIIa.

Scheme 1

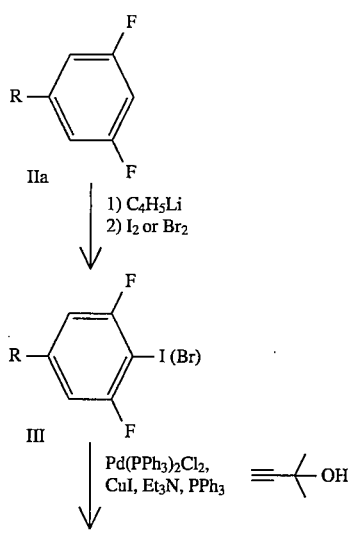

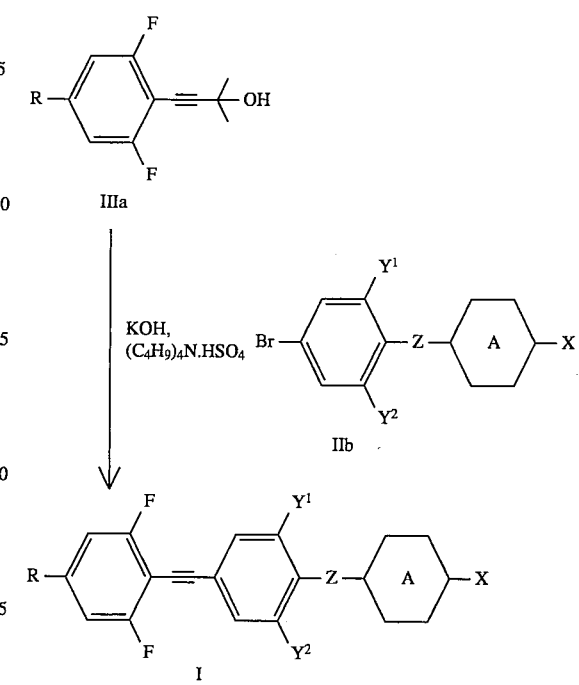

The starting materials of formula IIa are known or are analogues of known compounds. They can be prepared according to methods known per se, for example from commercially available 3,5-difluorobenzaldehyde by a Wittig reaction and subsequent hydrogenation or by etherification of likewise commercially available 3,5-difluorophenol. Suitable substituted phenyl derivatives of formula IIb are in many cases commercially available or can be modified readily from purchasable precursors according to methods known to a person skilled in the art.

The compounds of formula I are especially suitable for nematic mixtures, or, insofar as at least one component of the mixture is optically active, also for cholesteric mixtures. A preferred field of application is their use as dielectrics in liquid crystal indicating devices having a twisted nematic liquid crystal structure, such as TN cells, STN cells and TFT cells. Preferred mixtures are therefore those which additionally contain one or more compounds having a positive dielectric anisotropy.

The liquid crystalline mixtures in accordance with the invention contain at least two components, of which at least one component is a compound of formula I. A second component and optionally further components can be additional compounds of formula I and/or other liquid crystal components.

Having regard to the good solubility of the compounds of formula I in other liquid crystal materials and having regard to their good miscibility with one another, the content of the compounds of formula I in the mixtures in accordance with the invention can be relatively high and can be, for example, about 1–70 wt. %. In general, a content of about 3–40 wt. %, especially 5–30 wt. %, of compounds of formula I is preferred.

The mixtures in accordance with the invention preferably contain, in addition to one or more compounds of formula I, one or more compounds from the group of compounds of the formulas.

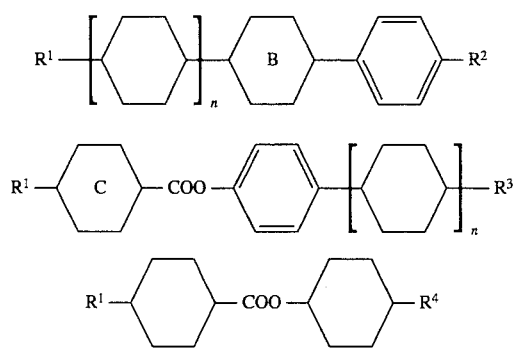
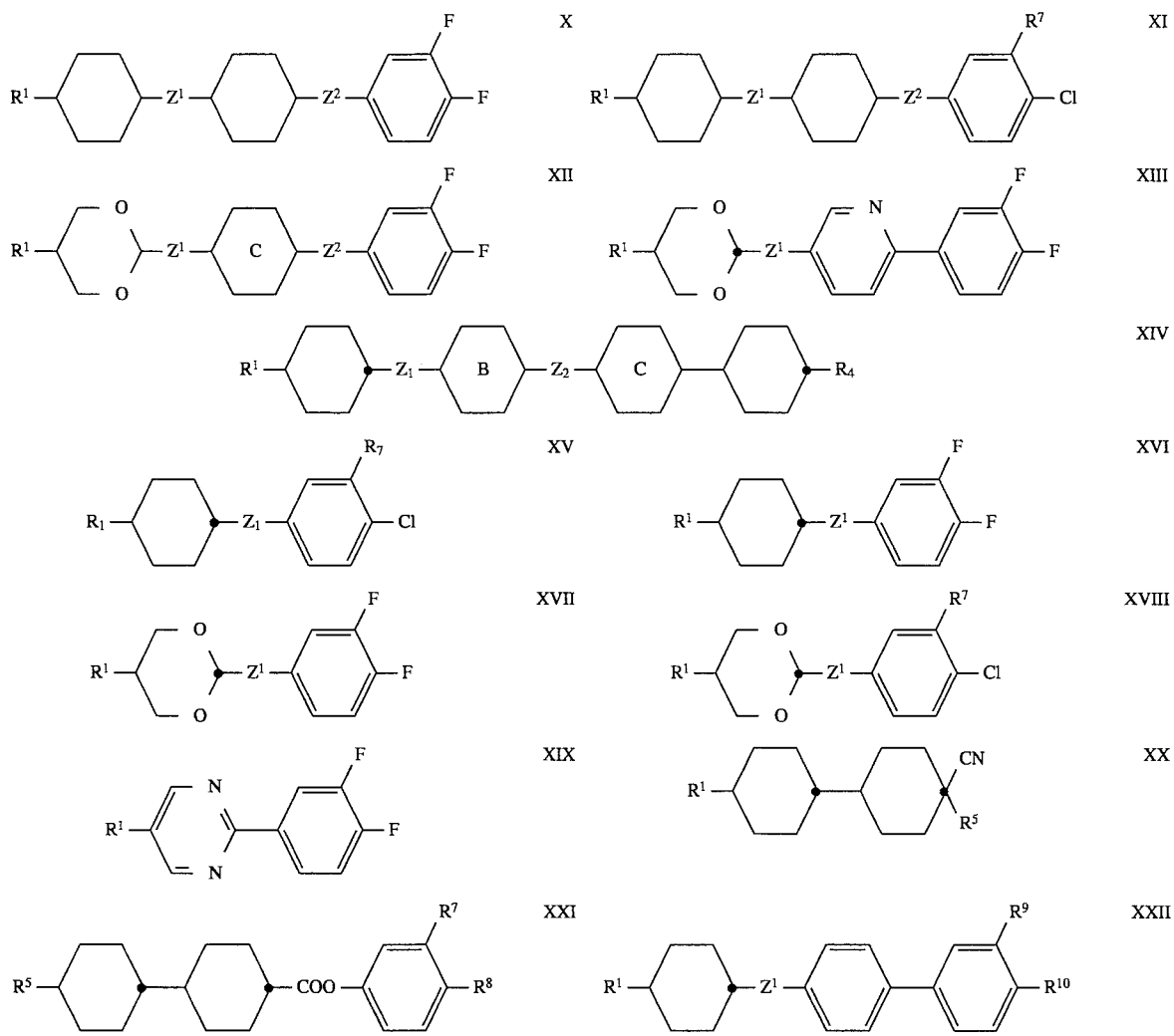

wherein $R^1$, $R^4$ is alkyl, alkoxyalkyl, 3E-alkenyl, 4-alkenyl or on saturated rings also 1E-alkenyl;

n is 0 or 1;

ring B is 1,4-phenylene, pyridine-2,5-diyl, pyrimidine-2,5-diyl, trans-1,4-cyclohexylene or trans-1,3-dioxane-2,5-diyl;

$R^2$ is cyano, isothiocyanto, fluorine, alkyl, 3E-alkenyl, 4-alkenyl, alkoxy, 2E-alkenyloxy, 3-alkenyloxy or 1-alkynyl;

ring C is 1,4-phenylene or trans-1,4-cyclohexylene;

$R^3$ is alkyl, 3E-alkenyl, 4-alkenyl or when Ring C is trans-1,4-cyclohexylene also 1E-alkenyl, or when Ring C is 1,4-phenylene also cyano, isothiocyanato, alkoxy, 2E-alkenyloxy or 3-alkenyloxy;

$R^5$ is alkyl, 1E-alkenyl, 3E-alkenyl or 4-alkenyl;

$R^6$ is cyano, alkyl, 1E-alkenyl, 3E-alkenyl, 4-alkenyl, alkoxy, 2E-alkenyloxy, 3-alkenyloxy, alkoxymethyl or (2E-alkenyl)oxymethyl;

$Z^1$, $Z^2$ each independently is a single covalent bond or —$CH_2CH_2$—, with two aromatic rings always being linked by a single covalent bond;

$R^7$ is hydrogen, fluorine or chlorine;

$R^8$ is cyano, fluorine or chlorine;

$R^9$ is hydrogen or fluorine; and $R^{10}$ is fluorine or chlorine.

For the above compounds of formulas IV to XXII, the following terms have the following meaning.

The above term "saturated ring" includes trans-1,4-cyclohexylene and trans-1,3-dioxane-2,5-diyl.

Each of the residues $R^1$ to $R^6$ preferably has 1 to 12 carbon atoms, especially 1 to 7 carbon atoms. Straight-chain residues are generally preferred.

The term "alkyl" preferably is in this connection straight-chain residues with 1 to 12 carbon atoms, preferably with 1 to 7 carbon atoms, such as, for example, methyl, ethyl, propyl, butyl, pentyl, hexyl or heptyl and the like.

The term "alkyloxyalkyl" preferably is in this connection straight-chain residues with 1 to 12 carbon atoms, especially with 1 to 7 carbon atoms, such as, for example, methoxymethyl, ethoxymethyl, propyloxymethyl, butyloxymethyl, methoxypropyl and the like.

The term "alkyloxy" preferably is in this connection straight-chain residues with 1 to 12 carbon atoms, especially with 1 to 7 carbon atoms, such as, for example, methoxy, ethoxy, propyloxy, butyloxy, pentyloxy, hexyloxy, heptyloxy and the like.

The term "1E-alkenyl" preferably is in this connection straight-chain alkenyl residues with 2 to 12, especially with 2 to 7, carbon atoms in which the double bond is situated in the 1-position, such as, for example, vinyl, 1E-propenyl, 1E-butenyl, 1E-pentenyl, 1E-hexenyl, 1E-heptenyl and the like.

The term "3E-alkenyl" preferably is in this connection straight-chain alkenyl residues with 4 to 12, especially with 4 to 7, carbon atoms in which the double bond is situated in the 3-position, such as, for example, 3-butenyl, 3E-pentenyl, 3E-hexenyl, 3E-heptenyl and the like.

The term "4-alkenyl" preferably is in this connection straight-chain alkenyl residues with 5 to 12 carbon atoms in which the double bond is situated in the 4-position, such as, for example, 4-pentenyl, 4-hexenyl, 4-heptenyl and the like.

The term "2E- or 3Z-alkenyloxy" preferably is in this connection straight-chain alkenyloxy residues with 3 or, respectively, 4 to 12 carbon atoms, especially with 3 or, respectively, 4 to 7 carbon atoms, in which the double bond is situated in the 2- or, respectively, 3-position and E or Z indicates the preferred configuration, such as, for example, allyloxy, 2E-butenyloxy, 2E-pentenyloxy, 2E-hexenyloxy, 2E-heptenyloxy, 3-butenyloxy, 3Z-pentenyloxy, 3Z-hexenyloxy, 3Z-heptenyloxy, 4-pentenyloxy, 5-hexenyloxy, 6-heptenyloxy and the like.

The term "1-alkynyl" preferably is in this connection straight-chain alkynyl residues with 2 to 12, especially with 2 to 7, carbon atoms in which the triple bond is situated in the 1-position, such as, for example, ethynyl, 1-propynyl, 1-butynyl, 1-pentynyl and the like.

The manufacture of the liquid crystalline mixtures and of the electro-optical devices can be effected in a manner known per se.

The invention is illustrated in more detail by the following Examples. In the Examples C is a crystalline phase, N is a nematic phase, S is a smectic phase and l is the isotropic phase. $V_{10}$ denotes the voltage for 10% transmission. $t_{on}$ and $t_{off}$ denote respectively the switching-on time and the switching-off time. $\Delta n$ denotes the optical anisotropy.

EXAMPLE 1 a) 22 ml of a 1.6N butyllithium solution in hexane were added dropwise during 30 min. to a solution of 5 g of 1-propyl-3,5-difluorobenzene in 50 ml of dry tetrahydrofuran at −70° C. and left to react at −70° C. for 1 hour. Then, a solution of 8.95 g of iodine in 20 ml of dry tetrahydrofuran was added dropwise at −60° within 10 minutes and the mixture was gradually warmed to room temperature within a further 30 minutes. The resulting yellow solution was then treated with 40 ml of a 10 percent aqueous sodium bicarbonate solution and extracted with ether. The ether solution was washed with saturated sodium chloride solution and several times with water, dried over magnesium sulphate, filtered and concentrated. Chromatography of the residue over 200 g of silica gel with hexane gave 1-propyl-3,5-difluoro-4-iodobenzene as a colourless liquid.

b) A mixture of 2 g of 1-propyl-3,5-difluoro-4-iodobenzene, 0.626 g of 2-methyl-3-butyn-2-ol, 0.164 g of tetrakis(triphenylphosphine)palladium(0), 10 ml of triethylamine and 0.054 g of copper(I) iodide was stirred at 90° for 2 hours. Then, the cooled reaction mixture was partitioned between water and ether, the ether phase was washed several times with water, dried over magnesium sulphate, filtered over Celite and evaporated on a rotary evaporator. The residue was then chromatographed on 75 g of silica gel (eluent: 10% ethyl acetate in hexane) and again evaporated. There were obtained 1.5 g of 4-(4-propyl-2,6-difluorophenyl)-2-methylbutyn-2-ol as a yellow liquid.

c) A mixture of 0.551 g of 4-(4-propyl-2,6-difluorophenyl)2-methylbutyn-2-ol, 0.68 g of 1-bromo-4-(4-trans-ethylcyclohexyl)benzene, 195 g of potassium hydroxide, 0.054 g of tetrakis(triphenylphosphine)palladium(0) and 5 ml of triethylamine was left to react under reflux for 16 hours. Then, the cooled reaction mixture was partitioned between water and ether, the ether phase was washed several times with water, dried over magnesium sulphate, filtered over Celite and evaporated on a rotary evaporator. The residue was then chromatographed on 100 g of silica gel with hexane. Two-fold crystallization from hexane gave 0.37 g of 2,6-difluoro-4-propyl-4'-(4-trans-ethylcyclohexyl)tolane. M.p. 55.6° C., cl.p. (N/l) 161.8° C.

The following compounds can be prepared in an analogous manner:
2,6-difluoro-4-ethyl-4'-(4-ethylphenyl)tolane;
2,6-difluoro-4-propyl-4'-(4-ethylphenyl)tolane;
2,6-difluoro-4-propyl-3'-fluoro-4'-(4-ethylphenyl)tolane;
2,6-difluoro-4-butyl-4'-(4-ethylphenyl)tolane;
2,6-difluoro-4-(3-butenyl)-4'-(4-ethylphenyl)tolane;
2,6-difluoro-4-pentyl-4'-(4-ethylphenyl)tolane;
2,6-difluoro-4-(4-pentenyl)-4'-(4-ethylphenyl)tolane;
2,6-difluoro-4-propyloxy-4'-(4-ethylphenyl)tolane;
2,6-difluoro-4-(3-butenyloxy)-4'-(4-ethylphenyl)tolane;
2,6-difluoro-4-ethyl-4'-(4-propylphenyl)tolane;
2,6-difluoro-4-propyl-4'-(4-propylphenyl)tolane;
2,6-difluoro-4-pentyl-4'-(4-propylphenyl)tolane;
2,6-difluoro-4-propyl-4'-(4-methoxyphenyl)tolane;
2,6-difluoro-4-butyl-4'-(4-ethoxyphenyl)tolane;
2,6-difluoro-4-propyl-4'-(3-fluoro-4-ethylphenyl)tolane;
2,6-difluoro-4-propyl-4'-(3-fluorophenyl)tolane;
2,6-difluoro-4-propyl-4'-(3-chlorophenyl)tolane;
2,6-difluoro-4-propyl-4'-(3,4-difluorophenyl)tolane;
2,6-difluoro-4-butyl-4'-(3,4-difluorophenyl)tolane;
2,6-difluoro-4-pentyl-4'-(3,4-difluorophenyl)tolane;
2,6-difluoro-4-(4-pentenyl)-4'-(3,4-difluorophenyl)tolane;
2,6-difluoro-4-propyl-4'-(4-trifluoromethylphenyl)tolane;
2,6-difluoro-4-propyl-4'-(3-fluoro-4-trifluoromethylphenyl)tolane;
2,6-difluoro-4-propyl-4'-(3-fluoro-4-chlorophenyl)tolane, m.p. (C/N) 70.7° C., cl.p. (N/l) 165.9° C.;
2,6-difluoro-4-propyl-4'-(4-difluoromethoxyphenyl)tolane;
2,6-difluoro-4-propyl-4'-(3-fluoro-4-difluoromethoxyphenyl)tolane;

2,6-difluoro-4-propyl-4'-(4-trifluoromethoxyphenyl)tolane;
2,6-difluoro-4-propyl-4'-[4-(2,2-difluorovinyl)phenyl]tolane;
2,6-difluoro-4-propyl-4'-[4-(2-fluorovinyl)phenyl]tolane;
2,6-difluoro-4-propyl-3'-fluoro-4'-[4-(2,2-difluorovinyl)phenyl]tolane;
2,6-difluoro-4-propyl-3'-fluoro-4'-[4-(2-fluorovinyl)phenyl]tolane;
2,6-difluoro-4-butyl-4'-(4-trans-ethylcyclohexyl)tolane;
2,6-difluoro-4-pentyl-4'-(4-trans-ethylcyclohexyl)tolane;
2,6-difluoro-4-propyloxy-4'-(4-trans-ethylcyclohexyl)tolane;
2,6-difluoro-4-propyl-4'-(4-trans-vinylcyclohexyl)tolane, m.p, (C/N) 56.3° C., cl.p. (N/l) 184.9° C.;
2,6-difluoro-4-propyl-4'-[4-trans-(2,2-difluorovinyl)cyclohexyl]tolane;
2,6-difluoro-4-propyl-4'-[4-trans-(2-fluorovinyl)cyclohexyl]tolane;
2,6-difluoro-4-propyl-4'-[4-trans-(2-E-chlorovinyl)cyclohexyl]tolane;
2,6-difluoro-4-propyl-4'-(4-trans-propylcyclohexyl)tolane;
2,6-difluoro-4-propyl-4'-[4-trans-(1-E-propenyl)cyclohexyl]tolane;
2,6-difluoro-4-propyl-4'-(4-trans-butylcyclohexyl)tolane;
2,6-difluoro-4-propyl-4'-[4-trans-(3-butenyl)cyclohexyl]tolane;
2,6-difluoro-4-butyl-4'-(4-trans-propylcyclohexyl)tolane;
2,6-difluoro-4-pentyl-4'-(4-trans-propylcyciohexyl)tolane;
2,6-difluoro-4-allyloxy-4'-(4-trans-propylcyclohexyl)tolane;
2,6-difluoro-4-propyl-4'-(4-trans-methoxycyclohexyl)tolane;
2,6-difluoro-4-propyl-4'-(4-trans-ethoxycyclohexyl)tolane;
2,6-difluoro-4-butyl-4'-(4-trans-ethoxycyclohexyl)tolane;
2,6-difluoro-4-pentyl-4'-(4-trans-methoxycyclohexyl)tolane;
2,6-difluoro-4-propyl-4'-(4-trans-allyloxycyclohexyl)tolane;
2,6-difluoro-4-propyl-4'-(4-trans-methoxymethylcyclohexyl)tolane;
2,6-difluoro-4-butyl-4'-(4-trans-methoxymethylcyclohexyl)tolane;
2,6-difluoro-4-pentyl-4'-(4-trans-methoxymethylcyclohexyl)tolane;
2,6-difluoro-4-propyl-4'-[2-(4-trans-ethylcyclohexyl)ethyl]tolane;
2,6-difluoro-4-butyl-4'-[2-(4-trans-ethylcyclohexyl)ethyl]tolane;
2,6-difluoro-4-pentyl-4'-[2-(4-trans-ethylcyclohexyl)ethyl]tolane;
2,6-difluoro-4-propyl-4'-[2-(4-trans-vinylcyclohexyl)ethyl]tolane;
2,6-difluoro-4-propyl-4'-{2-[4-trans-(2,2-difluorovinyl)cyclohexyl]ethyl}tolane;
2,6-difluoro-4-propyl-4'-{2-[4-trans-(2-fluorovinyl)cyclohexyl]ethyl}tolane;
2,6-difluoro-4-butyl-4'-{2-[4-trans-(2,2-difluorovinyl)cyclohexyl]ethyl}tolane;
2,6-difluoro-4-butyl-4'-{2-[4-trans-(2-fluorovinyl)cyclohexyl]ethyl}tolane;
2,6-difluoro-4-pentyl-4'-{2-[4-trans-(2,2-difluorovinyl)cyclohexyl]ethyl}tolane;
2,6-difluoro-4-pentyl-4'-{2-[4-trans-(2-fluorovinyl)cyclohexyl]ethyl}tolane;
2,6-difluoro-4-propyl-4'-{2-[4-trans-(2-E-chlorovinyl)cyclohexyl]ethyl}tolane;
2,6-difluoro-4-propyl-4'-[2-(4-trans-methoxycyclohexyl)ethyl]tolane;
2,6-difluoro-4-butyl-4'-[2-(4-trans-methoxycyclohexyl)ethyl]tolane;
2,6-difluoro-4-pentyl-4'-[2-(4-trans-methoxycyclohexyl)ethyl]tolane;
2,6-difluoro-4-propyl-4'-[2-(4-trans-ethoxycyclohexyl)ethyl]tolane;
2,6-difluoro-4-propyl-4'-[2-(4-trans-methoxymethylcyclohexyl)ethyl]tolane.

EXAMPLE 2

Binary mixtures (BM) with 4-(trans-4-pentylcyclohexyl)benzonitrile were prepared in order to investigate the properties of the compounds of formula (I) in mixtures. The threshold potential and the response times were measured at 22° C. in a TN cell (low bias tilt) having a plate separation of 8 mm; the 2.5-fold value of the threshold potential ($V_{10}$) was chosen as the operating voltage. The corresponding data for 4-(trans-4-pentylcyclohexyl)benzonitrile are: cl.p. (N/l)= 54.6° C., $V_{10}$=1.62 V, $t_{on}$=22 ms, $t_{off}$=42 ms, $\Delta n$=0.120.

BM-1

90 wt. % of 4-(trans-4-pentylcyclohexyl)benzonitrile 10 wt. % of 2,6-difluoro-4-propyl-4'-(3-fluoro-4-chlorophenyl)tolane;

cl.p. (N/l): 59° C., $V_{10}$=1.54 V, $t_{on}$=28 ms, $t_{off}$=46 ms, $\Delta n$=0.143.

BM-2

80 wt. % of 4-(trans-4-pentylcyclohexyl)benzonitrile 20 wt. % of 2,6-difluoro-4-propyl-4'-(3-fluoro-4-chlorophenyl)tolane;

cl.p. (N/l): 64.9° C., $V_{10}$=1.54 V, $t_{on}$=29 ms, $t_{off}$=48 ms, $\Delta n$=0.155.

BM-3

90 wt. % of 4-(trans-4-pentylcyclohexyl)benzonitrile 10 wt. % of 2,6-difluoro-4-propyl-4'-(4-trans-ethylcyclohexyl)tolane;

cl.p. (N/l): 59.6° C., $V_{10}$=1.52 V, $t_{on}$=27 ms, $t_{off}$=42 ms, $\Delta n$=0.133.

BM-4

80 wt. % of 4-(trans-4-pentylcyclohexyl)benzonitrile 20 wt. % of 2,6-difluoro-4-propyl-4'-(4-trans-ethylcyclohexyl)tolane;

cl.p. (N/l): 66.5° C., $V_{10}$=1.58 V, $t_{on}$=28 ms, $t_{off}$=43 ms, $\Delta n$=0.144.

BM-5

90 wt. % of 4-(trans-4-pentylcyclohexyl)benzonitrile 10 wt. % of 2,6-difluoro-4-propyl-4'-(4-trans-vinylcyclohexyl)tolane;

cl.p. (N/l): 61.6° C., $V_{10}$=1.50 V, $t_{on}$=25 ms, $t_{off}$=40 ms, $\Delta n$=0.135.

BM-6

80 wt. % of 4-(trans-4-pentylcyclohexyl)benzonitrile 20 wt. % of 2,6-difluoro-4-propyl-4'-(4-trans-vinylcyclohexyl)tolane;

cl.p. (N/l): 70.1° C., $V_{10}$=1.70 V, $t_{on}$=26 ms, $t_{off}$=42 ms, $\Delta n$=0,148.

We claim:
1. A compound of the formula

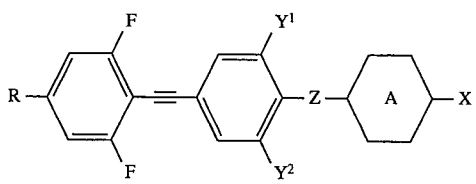

wherein
R is alkyl, alkoxy, alkenyl or alkenyloxy with up to 12 carbon atoms in which one $CH_2$ group can be replaced by oxygen and in which one or more hydrogen atoms can be replaced by fluorine atoms, with the proviso that two oxygen atoms are not directly adjacent;

$Y^1, Y^2$ each independently are fluorine or hydrogen;

A is unsubstituted or fluoro-substituted 1,4-phenylene;

Z is a single covalent bond; and

X is $CH=CF_2$, fluorine, chlorine, $-CF_3$, $-OCF_3$ or $-OCHF_2$.

2. A compound in accordance with claim 1, wherein one of the substituents $Y^1$ and $Y^2$ is hydrogen and the other is hydrogen or fluorine.

3. A compound in accordance with claim 2, wherein both substituents $Y^1$ and $Y^2$ are hydrogen.

4. A compound in accordance with claim 3, wherein X is fluorine or chlorine.

5. A compound in accordance with claim 3, wherein X is $-CH=CF_2$.

6. A compound in accordance with claim 3, wherein R is propyl, A is fluoro-substituted 1,4-phenylene, Z is a single covalent bond, and X is chlorine.

7. A compound in accordance with claim 1 of the formula

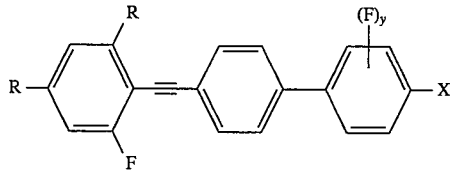

wherein
R is straight-chain alkyl, alkoxy, alkenyl or alkenyloxy with up to 6 carbon atoms in which one $CH_2$ group can be replaced by oxygen, with the proviso that two oxygen atoms are not directly adjacent;

X is fluorine, chlorine, $-OCF_3$, $-OCHF_2$, or $-CH=CF_2$;

y is 0, 1 or 2;

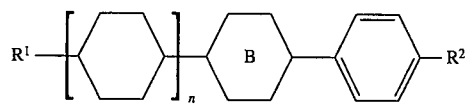

is unsubstituted or substituted as follows

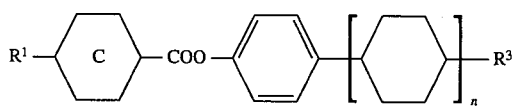

8. A liquid crystalline mixture comprising at least two components, a first component being a compound of the formula

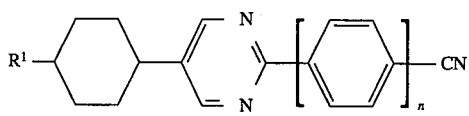

wherein
R is alkyl, alkoxy, alkenyl or alkenyloxy with up to 12 carbon atoms in which one $CH_2$ group can be replaced by oxygen and in which one or more hydrogen atoms can be replaced by fluorine atoms, with the proviso that two oxygen atoms are not directly adjacent;

$Y^1, Y^2$ each independently are fluorine or hydrogen;

A is unsubstituted or fluoro-substituted 1,4-phenylene;

Z is a single covalent bond; and

X is $CH=CF_2$, fluorine, chlorine, $-CF_3$, $-OCF_3$ or $-OCHF_2$, and a second component and optionally further components being selected from a group consisting of additional compounds of formula I and other liquid crystal components selected from a group consisting of compounds of formulas

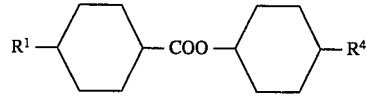

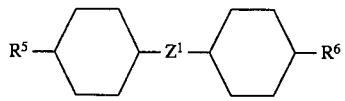

-continued

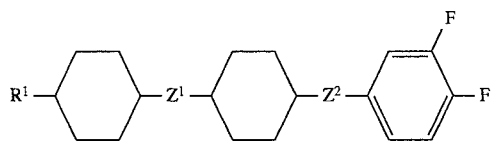 X

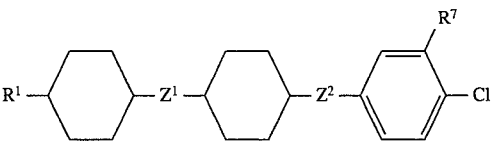 XI

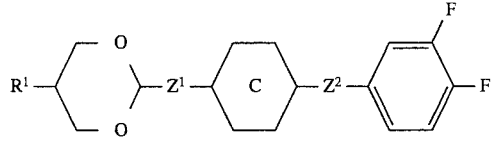 XII

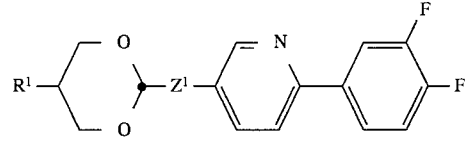 XIII

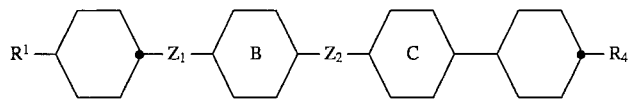 XIV

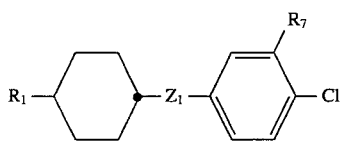 XV

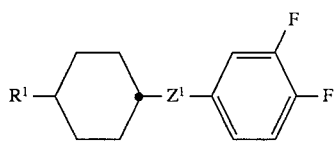 XVI

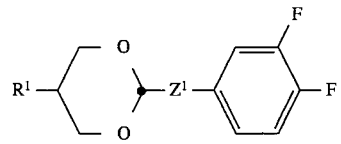 XVII

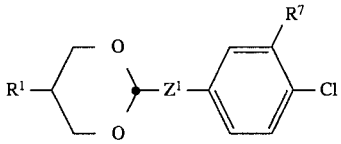 XVIII

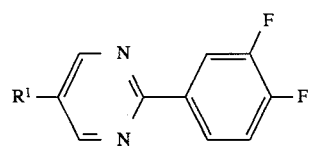 XIX

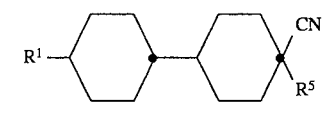 XX

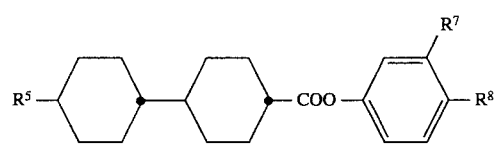 XXI

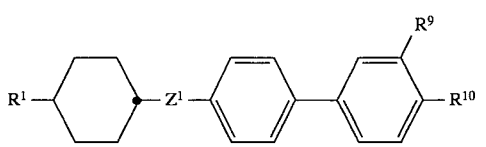 XXII wherein
- $R^1, R^4$ is alkyl, alkoxyalkyl, 3E-alkenyl, 4-alkenyl or on saturated rings also 1E-alkenyl;
- n is 0 or 1;
- ring B is 1,4-phenylene, pyridine-2,5-diyl, pyrimidine-2,5-diyl, trans,-1,4-cyclohexylene or trans-1,3-dioxane-2,5-diyl;
- $R^2$ is cyano, isothiocyanto, fluorine, alkyl, 3E-alkenyl, 4-alkenyl, alkoxy, 2E-alkenyloxy, 3-alkenyloxy or 1-alkynyl;
- ring C is 1,4-phenylene or trans-1,4-cyclohexylene;
- $R^3$ is alkyl, 3E-alkenyl, 4-alkenyl or when Ring C is trans-1,4-cyclohexylene also 1E-alkenyl, or when Ring C is 1,4-phenylene also cyano, isothiocyanato, alkoxy, 2E-alkenyloxy or 3-alkenyloxy;
- $R^5$ is alkyl, 1E-alkenyl, 3E-alkenyl or 4-alkenyl;
- $R^6$ is cyano, alkyl, 1E-alkenyl, 3E-alkenyl, 4-alkenyl, alkoxy, 2E-alkenyloxy, 3-alkenyloxy, alkoxymethyl or (2E-alkenyl)oxymethyl;
- $Z^1, Z^2$ each independently is a single covalent bond or —$CH_2CH_2$—, with two aromatic rings always being linked by a single covalent bond;
- $R^7$ is hydrogen, fluorine or chlorine;
- $R^8$ is cyano, fluorine or chlorine;
- $R^9$ is hydrogen or fluorine; and
- $R^{10}$ is fluorine or chlorine wherein each of the residues $R^1$ to $R^6$ has 1 to 12 carbon atoms.

9. A liquid crystalline mixture in accordance with claim 8, wherein the liquid crystalline mixture comprises 3–40 wt. % of the at least one component.

10. A liquid crystalline mixture in accordance with claim 9, wherein the liquid crystalline mixture comprises 5–30 wt. % of the at least one component.

11. An electro-optical device comprising a compound of the formula

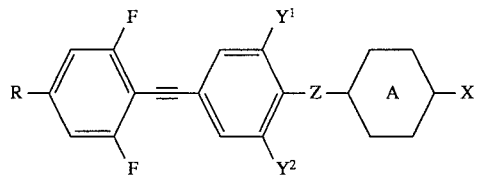 I wherein
- R is alkyl, alkoxy, alkenyl or alkenyloxy with up to 12 carbon atoms in which one $CH_2$ group can be replaced by oxygen and in which one or more hydrogen atoms can be replaced by fluorine atoms, with the proviso that two oxygen atoms are not directly adjacent;

$Y^1, Y^2$ each independently are fluorine or hydrogen;

A is unsubstituted or fluoro-substituted 1,4-phenylene;

Z is a single covalent bond; and

X is CH=CF$_2$, fluorine, chlorine, —CF$_3$, —OCF$_3$ or —OCHF$_2$.

12. An electro-optical device comprising a liquid crystalline mixture comprising at least two components, a first component being a compound of the formula

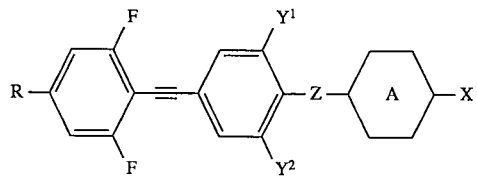
I wherein

R is alkyl, alkoxy, alkenyl or alkenyloxy with up to 12 carbon atoms in which one CH$_2$ group can be replaced by oxygen and in which one or more hydrogen atoms can be replaced by fluorine atoms, with the proviso that two oxygen atoms are not directly adjacent; $Y^1, Y^2$ each independently are fluorine or hydrogen;

A is unsubstituted or fluoro-substituted 1,4-phenylene;

Z is a single covalent bond; and

X is CH=CF$_2$, fluorine, chlorine, —CF$_3$, —OCF$_3$ or —OCHF$_2$, and a second component and optionally further components being selected from a group consisting of additional compounds of formula I and other liquid crystal components selected from a group consisting of compounds of formulas

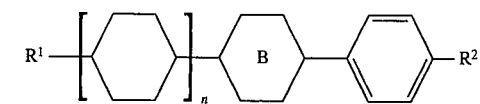
II

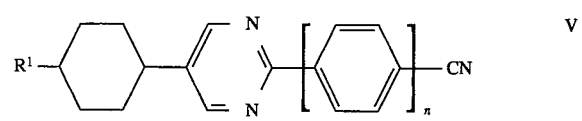
IV

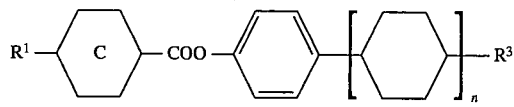
III

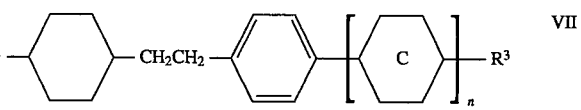
V

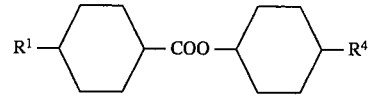
VI

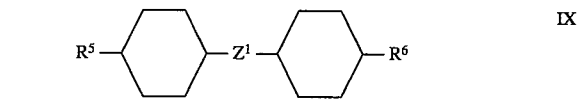
VII

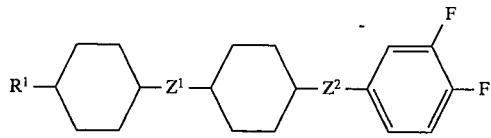
VIII

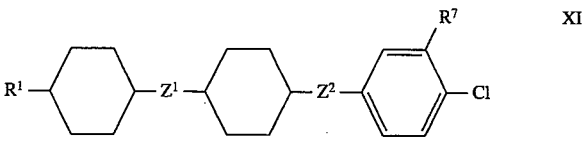
IX

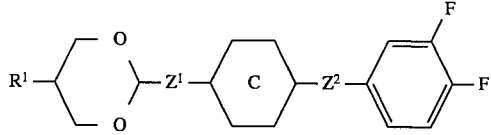
X

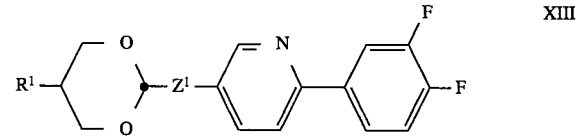
XI

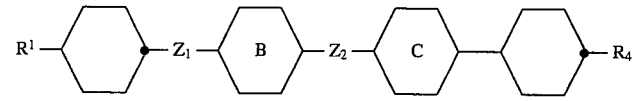

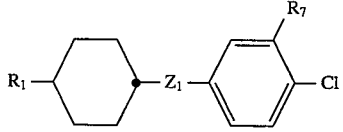
XII

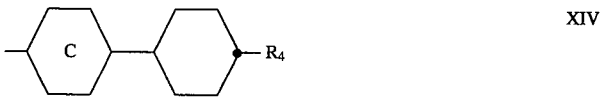
XIII

XIV

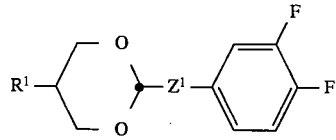
XV

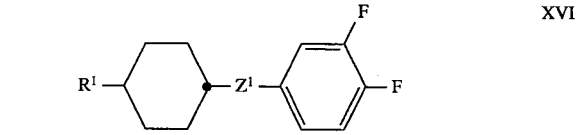
XVI

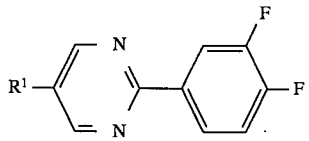
XVII

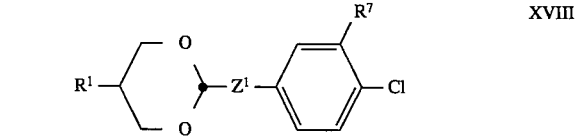
XVIII

XIX

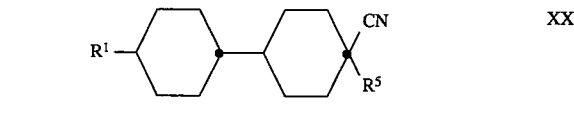
XX

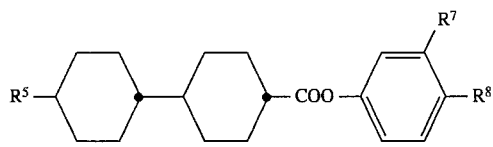 XXI

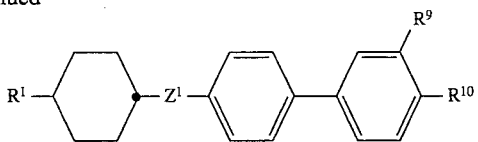 XXII wherein
- $R^1, R^4$ is alkyl, alkoxyalkyl, 3E-alkenyl, 4-alkenyl or on saturated rings also 1E-alkenyl;
- n is 0 or 1;
- ring B is 1,4-phenylene, pyridine-2,5-diyl, pyrimidine-2,5-diyl, trans,-1,4-cyclohexylene or trans-1,3-dioxane-2,5-diyl;
- $R^2$ is cyano, isothiocyanto, fluorine, alkyl, 3E-alkenyl, 4-alkenyl, alkoxy, 2E-alkenyloxy, 3-alkenyloxy or 1-alkynyl;
- ring C is 1,4-phenylene or trans-1,4-cyclohexylene;
- $R^3$ is alkyl, 3E-alkenyl, 4-alkenyl or when Ring C is trans-1,4-cyclohexylene also 1E-alkenyl, or when Ring C is 1,4-phenylene also cyano, isothiocyanato, alkoxy, 2E-alkenyloxy or 3-alkenyloxy;
- $R^5$ is alkyl, 1E-alkenyl, 3E-alkenyl or 4-alkenyl;
- $R^6$ is cyano, alkyl, 1E-alkenyl, 3E-alkenyl, 4-alkenyl, alkoxy, 2E-alkenyloxy, 3-alkenyloxy, alkoxymethyl or (2E-alkenyl)oxymethyl;
- $Z^1, Z^2$ each independently is a single covalent bond or $-CH_2CH_2-$, with two aromatic rings always being linked by a single covalent bond;
- $R^7$ is hydrogen, fluorine or chlorine;
- $R^8$ is cyano, fluorine or chlorine;
- $R^9$ is hydrogen or fluorine; and
- $R^{10}$ is fluorine or chlorine wherein each of the residues $R^1$ to $R^6$ has 1 to 12 carbon atoms.

\* \* \* \* \*